United States Patent [19]

Müller et al.

[11] 4,381,268
[45] Apr. 26, 1983

[54] DEVICE FOR GASSING LIQUIDS OR SUSPENSIONS

[75] Inventors: Gerhard Müller, Kelkheim; Günther Sell, Hattersheim am Main, both of Fed. Rep. of Germany

[73] Assignee: Hoechst Aktiengesellschaft, Frankfurt am Main, Fed. Rep. of Germany

[21] Appl. No.: 283,659

[22] Filed: Jul. 15, 1981

[30] Foreign Application Priority Data

Jul. 17, 1980 [DE] Fed. Rep. of Germany ....... 3027035

[51] Int. Cl.³ .............................................. B01F 3/04
[52] U.S. Cl. .................................. 261/109; 261/118; 239/433
[58] Field of Search ..................... 261/78 A, 118, 108, 261/109, DIG. 75, 117; 239/418, 433, 430, 502, 504, 524

[56] References Cited

U.S. PATENT DOCUMENTS

| | | | |
|---|---|---|---|
| 2,937,013 | 5/1960 | Fisher | 261/117 |
| 3,201,327 | 8/1965 | Beck | 261/117 |
| 3,364,880 | 1/1968 | Hoeven | 261/78 A |
| 3,421,692 | 1/1969 | Babington et al. | 261/30 |
| 3,601,374 | 8/1971 | Wheeler | 261/117 |
| 3,605,942 | 9/1971 | Lyth | 261/78 A |
| 3,737,106 | 6/1973 | Arnold et al. | 261/118 |
| 3,774,846 | 11/1973 | Schurig et al. | 261/78 A |
| 4,054,619 | 10/1977 | Coverston | 261/78 A |
| 4,305,894 | 12/1981 | Lindblom | 261/DIG. 75 |

FOREIGN PATENT DOCUMENTS

| | | | |
|---|---|---|---|
| 494237 | 5/1919 | France | 261/117 |
| 575293 | 4/1958 | Italy | 261/117 |
| 737735 | 6/1980 | U.S.S.R. | 239/418 |

*Primary Examiner*—Tim R. Miles
*Attorney, Agent, or Firm*—Curtis, Morris & Safford

[57] ABSTRACT

In a device for gassing liquids or suspensions, a first guide means is located at a short distance, opposite the orifice of a jet pipe. This guide means is supported via a gas inlet on a second guide means. The first guide means provided can be a cone and the second guide means can be a truncated cone which merges into a disc-shaped annular zone.

5 Claims, 1 Drawing Figure

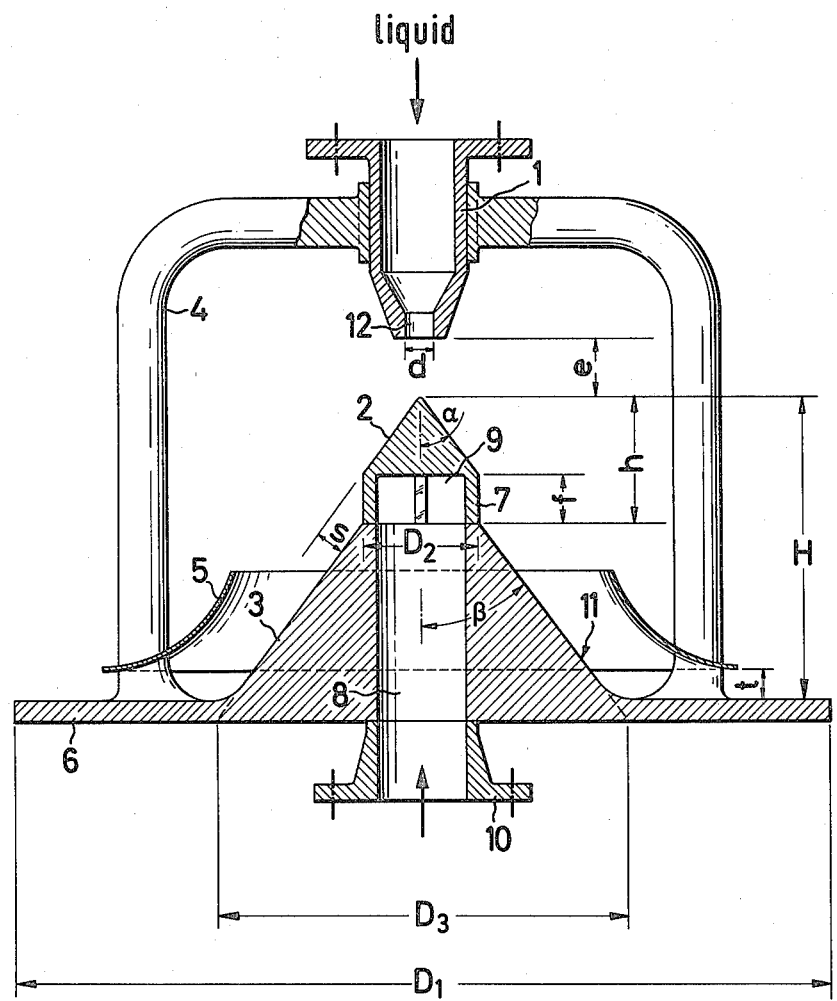

DEVICE FOR GASSING LIQUIDS OR SUSPENSIONS

The invention relates to a device for gassing liquids or suspensions in chemical or biological processes, for example in fermentation technology or effluent treatment technology.

In addition to simple gassing systems, such as, for example, single-component systems, devices have also been disclosed, for example two-component systems, such as injectors, ejectors, jet mixers, jet nozzles and the like, for gassing liquids or suspensions, wherein the kinetic energy of a liquid jet is utilized for dispersing the gas. All these have the disadvantage that their efficiency decreases rapidly when the device is made larger. In fact, the dispersion of the gas takes place predominantly in the edge zones of the liquid jet. When the volumetric flow is increased, the area of the edge zone does not correspondingly increase. A further disadvantage of the known gassing systems is the fact that the gas bubbles or the liquid/bubble mixture are not adequately mixed into the surrounding liquid, as a result of which the coalescence of bubbles is promoted.

Accordingly, it is the object of the invention to provide a device which, largely independently of its size, makes possible an improved dispersion and distribution of the gas bubbles in liquids and suspensions.

The object is achieved by a device, wherein a first guide means is located, at a short distance, opposite the orifice of a jet pipe and is supported via a gas inlet on a second guide means.

The first guide means provided can be a cone and the second guide means can be a truncated cone, it being possible to select the distance between the guide means to be 3 to 50 mm and the diameter of the cone to be 1 to 10% greater than the smaller diameter of the truncated cone. In place of a cone having a straight generating line, a cone having a concave generating line is also possible. The cone angle of the truncated cone can be 0° to 20° greater than the cone angle of the cone. The shell of the truncated cone can merge asymptotically into the base of the truncated cone, that is to say it can have a steady transition into a disc-shaped annular zone. The size of this disc-shaped annular zone can be a multiple of the base of the truncated cone. Around the truncated cone, a guide element can be arranged, the distance of which from the shell of the truncated cone decreases with increasing diameter.

The liquid jet is torn apart by the two guide means to give a film which flows off obliquely or radially, the gas bubbles being formed in the interface of the film due to the shear forces. At the same time, the bubbles/liquid mixture is uniformly mixed into the liquid or suspension which is to be gassed.

In the following text, the invention is explained in more detail by reference to the drawing which diagrammatically shows the construction of the device in an exemplary embodiment.

The gassing device comprises a jet pipe (1), the two guide means (2 and 3) and the gas inlet (7). The jet pipe (1) is arranged above the guide means (2), for example a cone having an angle of $\alpha = 5°$ to 89° or a plate, or a combination of the two, in such a way that the jet is torn apart as symmetrically as possible by the guide means (2) to give a liquid film which is steadily enlarged up to the tear-off edge of the guide means (2). The distance e between the jet pipe (1) and the guide means (2) can be zero to 5d, preferably 2d, d being the diameter of the outlet orifice (12) of the jet pipe (1). The diameter d of the outlet orifice (12) is selected in accordance with the quantities of liquid which are to be put through. Diameters of between 20 and 40 mm have proved to be utilizable. Relative to the guide means (2), the jet pipe (1) is fixed by means of brackets (4) which are arranged on the guide means (3). The guide means (2) is located on the gas inlet (7) which is supported on the guide means (3). The guide means (3) is provided with a bore (8) which is connected to the gas inlet (7), for example a cylindrical ring with orifices (9). (10) indicates a flange for connection to a gas line. The dimensions of the second guide means (3) are such that, between its surface and the liquid film coming from the first guide means (2), an annular gap can form which has the thickness s and into which the gas is drawn via the gas inlet (7). The thickness of the annular gap is determined by the gas rate. The ratio of the thickness s of the gap to the distance $f = 3$ to 50 mm of the two guide means (2 and 3) from one another should be 0.1 to 1. The gas velocity in the annular gap should not be higher than 50 m/second. Intense thorough mixing of jet liquid and gas, and hence the formation of bubbles, take place in the liquid interface and on the surface of the second guide means (3). The liquid film is also steadily enlarged on the second guide means (3). Moreover, secondary liquid is drawn in and is also mixed with the gas. If a truncated cone is used as the guide means (3), it has proved to be advantageous when the shell (11) asymptotically merges into a disc-shaped annular zone (6). The liquid/bubbles mixture is introduced horizontally via this annular zone into the liquid or suspension which is to be gassed, substantially uniform gassing thus becoming possible. It can be advantageous to provide a guide element (5) around the guide means (3), as a result of which, in non-coalescing systems, for example alcohol/water mixtures, bubbles having a smaller diameter can be produced than in coalescing systems (water), with the same consumption of energy. It is expedient to reduce the distance of the guide element (5) from the surface of the guide means (3) with increasing diameter, in which case the ratio of the largest diameter $D_3$ of the guide means (3) to the shortest distance t of the guide element (5) from the surface of the guide means (3) should be 3 to 30. The ratio of the diameter $D_1$ of the disc-shaped annular zone (6) to the diameter d of the jet pipe orifice (12) can be 5 to 100 and that of the diameter $D_2$ of the guide means (2) to d can be 2 to 20. The ratio of the height h, which is the sum of the heights of the guide means (2) and of the gas inlet (7), to the height H, which is the sum of the height of the guide means (3) and the height h, can be 0.01 to 1.

We claim:

1. A device for gassing liquids which comprises an inlet having a jet orifice for projecting a coherent jet of liquid, a conical surface substantially without obstructions thereon opposite the orifice for piercing the jet of liquid and inducing flow of a liquid film over the conical surface, a frustro-conical surface under the conical surface and spaced therefrom to cause liquid flowing over the conical surface to continue its flow over the frustro-conical surface at a distance therefrom, means for introducing a stream of gas or vapor into the space between the conical and frustro-conical surfaces for intimate admixture with the flow of liquid thereover, and guide means spaced from the base of the frustro-conical surface forming an annular zone for withdrawing gassed liquid therefrom.

2. A device as defined in claim 1 wherein the spacing between the conical and frusto-conical surfaces is from 3 to 50 mm and the maximum diameter of the conical surface is from 1 to 10% greater than the minimum diameter of the frusto-conical surface.

3. A device as defined in claim 1 wherein the angle of the frusto-conical surface with the vertical axis thereof is 0° to 20° greater than the angle of the conical surface with said vertical axis.

4. A device as defined in claim 1 wherein the base of the frusto-conical surface merges asymptotically into a dish-shaped annular zone.

5. A device as defined in claim 1 wherein the spacing of the guide means from the base of the frusto-conical surface decreases as the diameter of the frusto-conical surface increases.

* * * * *